United States Patent [19]

Simon

[11] Patent Number: 5,795,878
[45] Date of Patent: Aug. 18, 1998

[54] BIOCIDAL COMPOUNDS THEIR PREPARATION AND USE

[75] Inventor: Werner Simon, Hüffelsheim, Germany

[73] Assignee: American Cyanamid Company, Madison, N.J.

[21] Appl. No.: 871,016

[22] Filed: Jun. 6, 1997

Related U.S. Application Data

[60] Provisional application No. 60/019,979, Jun. 17, 1996.
[51] Int. Cl.⁶ .......................... A01N 41/06; C07C 311/20
[52] U.S. Cl. .......................... 514/149; 534/556; 534/566; 534/572; 534/557
[58] Field of Search .......................... 514/149; 534/556, 534/557, 566, 572

[56] References Cited

U.S. PATENT DOCUMENTS

| | | | |
|---|---|---|---|
| 5,273,997 | 12/1993 | Naisby et al. | 514/452 |
| 5,439,897 | 8/1995 | Simon | 514/149 |
| 5,475,093 | 12/1995 | Simon | 534/572 |

FOREIGN PATENT DOCUMENTS

| | | |
|---|---|---|
| 411720 | 2/1991 | European Pat. Off. . |
| 645384 | 3/1995 | European Pat. Off. . |

OTHER PUBLICATIONS

Umeda et al., "Antimicrobial Phenylazoxycyanides", Chemical Abstracts, 87:16770 (1977).

*Primary Examiner*—Fiona T. Powers
*Attorney, Agent, or Firm*—Charles F. Costello, Jr.

[57] ABSTRACT

A phenylazoxycyanide compound of formula I

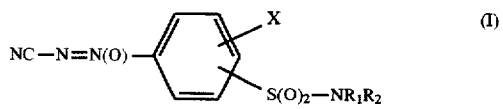

is useful as an antimicrobial and fungicidal composition. A method for using the antimicrobial and fungicidal compositions, and for manufacturing the compound is also disclosed.

18 Claims, No Drawings

BIOCIDAL COMPOUNDS THEIR PREPARATION AND USE

This application claims priority from copending provisional application Ser. No. 60/019979 filed on Jun. 17, 1996.

BACKGROUND OF THE INVENTION

Plant cultivation in agriculture and in horticulture is often threatened and damaged by pests and disease, such as disease caused by a variety of phytopathogenic fungi. To shield foods, crops and ornamental plants from fungal disease and to control such disease, many types of fungicides have been suggested. Phytopathogenic fungi often develop resistance to certain fungicidal agents after several years of application. Therefore, there is a permanent demand for new highly effective fungicides.

Various fungicidal compounds with considerable activity against phytopathogenic fungi have been found to cause phytotoxic damage when applied to the plants at disease control rates.

The prior art includes amidosulphonylphenylazoxycyanides of formula (A)

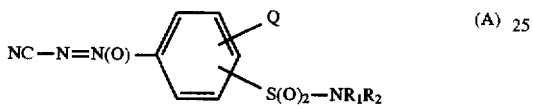

wherein Q represents a hydrogen or halogen atom and each of $R_1$ and $R_2$ independently represents a hydrogen atom, an optionally substituted phenyl or alkyl group or together may represent an alkylene chain which is optionally interrupted by an oxygen atom. These compounds are effective against a broad spectrum of phytopathogenic fungi. However, they are not completely satisfactory as fungicidal agents because of phytotoxic properties which may appear in unfavourable circumstances.

Therefore, it is an object of this invention to provide a method for controlling undesired fungi without causing phytotoxic injury.

It is another object of this invention to provide a fungicidal composition with little or no phytotoxic properties.

It is a further object of this invention to provide arylazoxycyanide compounds useful as non-phytotoxic fungicidal compounds.

These and other objects and features of the invention will become more apparent from the detailed description set forth hereinbelow.

SUMMARY OF THE INVENTION

The present invention provides highly effective fungicidal phenylazoxycyanides of formula I which do not cause phytotoxic damage to the host plants when applied at disease control rates. Said phenylazoxycyanides are compounds of formula (I)

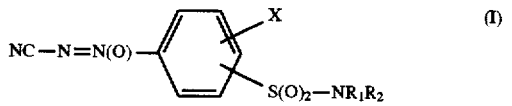

wherein $R_1$ represents a hydrogen atom or a $C_1$–$C_4$alkyl group;

$R_2$ represents a $C_3$–$C_8$cycloalkyl group, which may be substituted by one to three $C_1$–$C_6$alkyl groups or may be condensed with a benzene or a cyclohexane ring; and X represents a hydrogen, fluorine, chlorine or bromine atom or a $C_1$–$C_6$alkyl group. Said formula I compounds show excellent antimicrobial, particularly fungicidal, activity combined with low, uncritical phytotoxicity.

Also provided are methods and compositions useful for non-phytotoxic control of phytopathogenic fungi.

Specific embodiments of the invention are as follows:

1. A compound comprising formula (I):

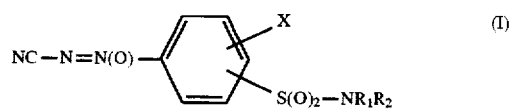

wherein $R_1$ represents a hydrogen atom or a $C_1$–$C_4$alkyl group;

$R_2$ represents a $C_3$–$C_8$cycloalkyl group, which may be substituted by one to three $C_1$–$C_6$alkyl groups or may be condensed with a benzene or a cyclohexane ring; and X represents a hydrogen, fluorine, chlorine or bromine atom or a $C_1$–$C_6$alkyl group.

2. The compound of embodiment 1, wherein X represents a hydrogen atom.

3. The compound of embodiment 1, wherein $R_1$ represents a hydrogen atom.

4. The compound of embodiment 1, wherein $R_1$ and X each represent a hydrogen atom.

5. The compound of embodiment 4, selected from the group consisting of
   4-(N-cyclopropylamidosulphonyl)phenylazoxycyanide;
   4-(N-cyclobutylamidosulphonyl)phenylazoxycyanide;
   4-(N-cyclopentylamidosulphonyl)phenylazoxycyanide;
   4-(N-cyclohexylamidosulphonyl)phenylazoxycyanide;
   4-(N-cycloheptylamidosulphonyl)phenylazoxycyanide;
   4-(N-cyclooctylamidosulphonyl)phenylazoxycyanide;
   4-(N-4-methylcyclohexylamidosulphonyl)phenylazoxycyanide;
   4-(N-1-tetralineamidosulphonyl)phenylazoxycyanide; and
   4-(N-methyl-N-cyclohexylamidosulphonyl)phenylazoxycyanide.

6. A compound comprising formula Ia:

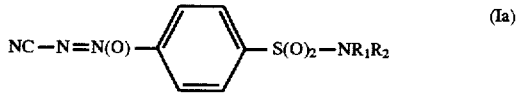

wherein $R_1$ represents a hydrogen atom or a $C_1$–$C_4$alkyl group; and $R_2$ represents a $C_3$–$C_8$cycloalkyl group, which may be substituted by one to three $C_1$–$C_6$alkyl groups or may be condensed with a benzene or a cyclohexane ring.

7. An antimicrobial composition of embodiment 1, having an antimicrobially effective amount of the composition of formula I.

8. The antimicrobial composition of embodiment 7, wherein X represents a hydrogen atom.

9. A fungicidal composition of embodiment 1 having a fungicidally effective amount of the composition of formula I and an agriculturally acceptable carrier.

10. The fungicidal composition of embodiment 9, wherein X represents a hydrogen atom.

11. The fungicidal composition of embodiment 9, wherein $R_1$ represents a hydrogen atom.

12. The fungicidal composition of embodiment 9, wherein $R_1$ and X each represent a hydrogen atom.

13. The fungicidal composition of claim 12 selected from the group consisting of
   4-(N-cyclopropylamidosulphonyl) phenylazoxycyanide;
   4-(N-cyclobutylamidosulphonyl)phenylazoxycyanide;
   4-(N-cyclopentylamidosulphonyl) phenylazoxycyanide;
   4-(N-cyclohexylamidosulphonyl)phenylazoxycyanide;
   4-(N-cycloheptylamidosulphonyl) phenylazoxycyanide;
   4-(N-cyclooctylamidosulphonyl)phenylazoxycyanide;
   4-(N-4-methylcyclohexylamidosulphonyl) phenylazoxycyanide;
   4-(N-1-tetralineamidosulphonyl)phenylazoxycyanide; and
   4-(N-methyl-N-cyclohexylamidosulphonyl) phenylazoxycyanide.

14. A fungicidal composition of embodiment 6 having a fungicidally effective amount of the compound of formula Ia.

15. A method for combating an undesired microorganism, which comprises treating a locus infected therewith with the antimicrobial composition of embodiment 7.

16. A method for combating a phytopathogenic fungi, which method comprises contacting the phytopathogenic fungi with a fungicidally effective amount of the composition of embodiment 9.

17. The method according to embodiment 16 wherein $R_1$ and X each represent a hydrogen atom.

18. A process for the preparation of a compound of formula I

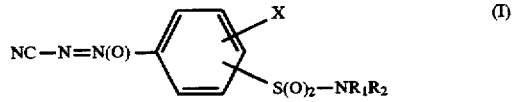

wherein $R_1$ represents a hydrogen atom or a $C_1$–$C_4$alkyl group; $R_2$ represents a $C_3$–$C_8$cycloalkyl group, which may be substituted by one to three $C_1$–$C_6$alkyl groups or may be condensed with a benzene or a cyclohexane ring; and X represents a hydrogen, fluorine, chlorine or bromine atom or a $C_1$–$C_6$alkyl group, the process comprising
treating a nitroso compound of formula II

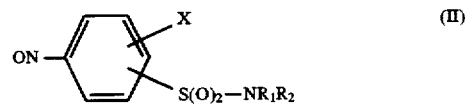

with N-bromosuccinimide and with sodium cyanamide.

DETAILED DESCRIPTION OF THE INVENTION

It has now been found that formula (I) phenylazoxycyanides

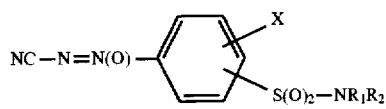

wherein $R_1$ represents a hydrogen atom or a $C_1$–$C_4$alkyl group;

$R_2$ represents a $C_3$–$C_8$cycloalkyl group, which may be substituted by one to three $C_1$–$C_6$alkyl groups or may be condensed with a benzene or a cyclohexane ring; and X represents a hydrogen, fluorine, chlorine or bromine atom or a $C_1$–$C_6$alkyl group demonstrate an excellent antimicrobial, particularly fungicidal, activity combined with low, in practice, uncritical phytotoxicity.

Within the above definitions, the alkyl groups may be straight or branched and the number of carbon atoms contained therein is preferably up to 4. The cycloalkyl groups represented by $R_2$ may contain as substituents 1, 2 or 3 alkyl groups, preferably methyl or ethyl groups. If two or more alkyl groups are present in a compound of formula I, the number of carbon atoms therein is independent from each other.

X is preferably a hydrogen atom, a methyl or ethyl group or a fluorine or chlorine atom. Most preferred are compounds of formula I wherein X is a hydrogen atom. The amidosulphonyl group is preferably in the 4-position relative to the azoxycyanide moiety.

The azoxycyanide group can exist in several isoelectronic forms; the formula for the azoxycyanide moiety used in the formulae in this application shall cover any such forms and the various formulae shall also cover any other types of isomers.

A preferred group of compounds of formula I are those represented by formula Ia

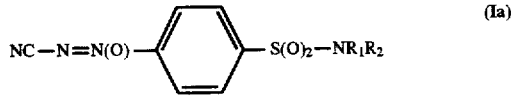

wherein $R_1$ and $R_2$ are defined hereinabove for formula I.

Typical compounds according to the invention include, but are not limited to:
  4-(N-cyclopropylamidosulphonyl)phenylazoxycyanide;
  4-(N-cyclobutylamidosulphonyl)phenylazoxycyanide;
  4-(N-cyclopentylamidosulphonyl)phenylazoxycyanide;
  4-(N-cyclohexylamidosulphonyl)phenylazoxycyanide;
  4-(N-cycloheptylamidosulphonyl)phenylazoxycyanide;
  4-(N-cyclooctylamidosulphonyl)phenylazoxycyanide;
  4-(N-4-methylcyclohexylamidosulphonyl) phenylazoxycyanide;
  4-(N-1-tetralineamidosulphonyl)phenylazoxycyanide;
  4-(N-methyl-N-cyclohexylamidosulphonyl) phenylazoxycyanide; and the like.

Compounds of the invention may be prepared according to known methods such as those described in U.S. Pat. No. 5,475,093, which is incorporated herein by reference. Suitable starting materials are nitroso compounds of formula II

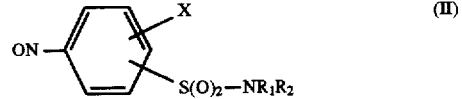

which may be converted to the corresponding azoxycyanide by reacting said formula II compound with N-bromosuccinimide in a polar solvent, such as dimethylformamide, preferably at ambient temperatures, subsequently treating the reaction mixture slowly with sodium cyanamide with stirring at ambient temperatures, diluting the resultant mixture with water, and isolating the desired azoxycyanide product by standard procedures such as extraction or filtration.

The formula II nitroso compound starting material may be prepared according to known methods such as those described in published European patent application 411,720, which is incorporated herein by reference. For example, starting from the corresponding nitro compound the nitro group may be reduced by means of hydrazine hydrate in the presence of a catalyst such as rhodium/carbon and a solvent. The resultant hydroxylamine product may then be oxidised, e.g. with $FeCl_3$, to give the nitroso compound of formula II.

The phenylazoxycyanide compounds of the invention are particularly useful for combating or controlling a wide spectrum of phytopathogenic fungi, such as *Plasmopara viticola, Botrytis cinerea, Alternaria solani, Phytophthora infestans, Venturia inaequalis, Leptosphaeria nodorum*, and the like. Thus the compounds can be used for the treatment of plant diseases caused by said fungi in many plant cultures e.g. in vine, apples, tomatoes, potatoes, cereal crops, and the like.

Therefore, there is provided a method of combating phytopathogenic fungi which comprises treating the fungi or the locus thereof with a fungicidally effective amount of a compound of formula I. The locus may be an agricultural or horticultural locus, for example plants, plant seeds or the medium in which said plants or seeds are growing or are to be grown or are stored.

In actual practice, fungicidally effective amounts will vary according to the prevailing conditions such as the nature of the disease, degree of infection, plant species, plant size, mode of application, weather, soil and the like. A locus described above may suitably be treated with a compound of formula I at an application rate of about 0.04 kg/ha to 4.0 kg/ha, preferably about 0.1 kg/ha to 1.0 kg/ha.

The present invention further provides a biocidal, particularly fungicidal, composition which comprises a fungicidally effective amount of a compound of formula I or Ia as defined hereinabove and an agriculturally acceptable carrier. The composition of the invention may contain one or more compounds of formulae I or Ia. Preferably, at least one carrier in a composition according to the invention is a surface-active agent. For example, the composition may contain at least two carriers, at least one of which is a surface-active agent.

The compounds according to formula I or Ia may also be applied directly as technical material, however, said compounds are preferably applied as a composition comprising, besides the formula I or Ia compounds, adjuvants and auxiliaries which are known for formulation purposes. Said compositions may be formulated as emulsion concentrates, trates, solutions which may be sprayed directly or diluted, luted, diluted emulsions, wettable powders, soluble powders, dusts, granulates, microencapsulates and the like. The form of application such as spraying, atomizing, dispersing, pouring, and the like may be chosen, like the compositions, according to the desired objectives and the given circumstances.

It is contemplated, compounds of formula I or Ia may be formulated or applied, either alone or in combination, with one or more pesticides or plant growth regulants. Pesticides used in combination may be insecticides, acaricides or other fungicides or a combination thereof. When the formula I or Ia compounds are applied in combination with another pesticide or pesticides, they may be applied simultaneously or sequentially. Among the available fungicides which may be used in combination with the formula I compounds of the invention are 4,6-dinitro-o-cresol, benalaxyl, benomyl, captafol, captan, carbendazim, chlorothalonil, copper, cymoxanil, dichlofluanid, dichlone, difenoconazole, dimethomorph, diniconzole, dinocap, dithianon, fenpiclonil, fenpropiomorph, hymaxazol, imazalil, iprodione, isoprothiolane, kasugamycin, mancozeb, mepronil, mercuric oxide, oxadixyl, oxolinic acid, penconazole, propineb, pyrifenox, thiabendazole, thiram, tolclofos-methyl, triadimefon, triflumizole, triforine validamycin A, vinclozolin, zineb, ziram, and the like.

The fungicidal compositions of the invention may be prepared by well-established procedures, e.g. intensive mixing and/or grinding of the active ingredients with other substances, such as fillers, solvents, solid carriers, and optionally surface-active compounds (tensides).

Solvents may be aromatic hydrocarbons, preferably the fractions $C_8$ to $C_{12}$, e.g. xylenes or xylene mixtures, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl 2-pyrrolidone, dimethyl sulphoxide, alkyl formamides, epoxidized vegetable oils, e.g. epoxidized coconut or soybean oil, water and the like.

Solid carriers, which may be used for dusts or dispersible powders, may be mineral fillers, such as calcite, talc, kaolin, montmorillonite, attapulgite. The physical properties may be improved by addition of highly dispersed silica gel or highly dispersed polymers.

Solid carriers for granulates may be porous material, e.g. pumice, broken brick, sepiolite, bentonite, non-sorptive carriers may be calcite or sand and the like. Additionally, a multitude of pre-granulated inorganic or organic materials may be used, such as dolomite or crushed plant residues.

Suitable surface-active substances may be nonionogenic, anionic or cationic tensides with good dispersing, emulgating and wetting properties depending on the nature of the azoxycyanide compound to be formulated. Tensides may also mean mixtures of tensides.

Suitable tensides may be so-called water-soluble soaps as well as water-soluble synthetic surface-active compounds. Soaps usually are alkali, earth alkali or optionally substituted ammonium salts of higher fatty acids ($C_{10}$–$C_{20}$), e.g. the sodium or potassium salts of oleic or stearic acid or of mixtures of natural fatty acids which are prepared, for example, from coconut or tallow oil. Furthermore, methyltaurine salts of fatty acids may be used. However, so-called synthetic tensides are preferably used, especially fatty sulphonates, fatty sulphates, sulphqnated benzimidazole derivatives or alkyl aryl sulphonates. The fatty sulphates or fatty sulphonates onates are normally used as alkali, earth alkali or optionally substituted ammonium salts and have an alkyl moiety of 8 to 22 carbon atoms, whereby alkyl also means the alkyl moiety of acyl residues, such as the sodium or calcium salt of lignin sulphonic acid, of sulphuric acid dodecylate or of a mixture of fatty alcohols prepared from natural fatty acids. This also includes the salts of sulphuric acid esters, sulphonic acids and adducts of fatty alcohols and ethylene oxide. The sulphonated benzimidazole derivatives preferably contain 2 sulphonic acid residues and a fatty acid residue with 8 to 22 carbon atoms. Alkyl aryl sulphonates are, for example, the sodium, calcium or triethyl ammonium salts of dodecyl benzene sulphonic acid, dibutyl naphthalene sulphonic acid or of a condensate of naphthalene sulphonic acid and formaldehyde. Furthermore, phosphates, such as the salts of the phosphoric acid ester of a p-nonylphenol-(4-14)-ethylene oxide adduct or phospholipids, may be used.

Non-ionic tensides are preferably polyglycolether derivatives of aliphatic or cycloaliphatic alcohols, saturated or non-saturated fatty acids and alkylphenols, which have 3 to 10 glycol ether groups and 8 to 20 carbon atoms in the (aliphatic) hydrocarbon residue and 6 to 18 carbon atoms in the alkyl residue of the alkyl phenols. Other suitable non-ionic tensides are the water-soluble, 20 to 250 ethylene glycol ether groups containing polyadducts of ethylene oxide and polypropylene glycol, ethylene diamino polypropylene glycol and alkyl polypropylene glycol with 1 to 10 carbon atoms in the alkyl moiety, the substances normally contain 1 to 5 ethylene glycol units per propylene glycol unit. Examples of non-ionic tensides are nonylphenol polyethoxy ethanols, castor oil polyglycol ether, polyadducts of ethylene oxide and polypropylene, tributyl phenoxy polyethoxy ethanol, polyethylene glycol, octyl phenoxy polyethoxy ethanol. Furthermore, fatty acid esters of polyoxy ethylene sorbitan, such as polyoxy ethylene sorbitan trioleate may be used.

Cationic tensides preferably are quaternary ammonium salts, which have at least one alkyl residue with 8 to 22 carbon atoms and, furthermore, low, optionally-halogenated alkyl, benzyl or hydroxyalkyl residues. The salts are preferably halides, methyl sulphates or alkyl sulphates, e.g. stearyl trimethyl ammonium chloride or benzyl bis(2-chloroethyl) ethyl ammonium bromide.

The tensides generally used for compositions of the invention are disclosed in publications such as:

"McCutheon's Detergents and Emulsifiers Annual", MC Publishing Corp., Ridgewood, N.J., USA 1981;

H. Stache, "Tensid-Taschenbuch", 2nd ed., C. Hanser, Munich, Vienna, 1981;

M. and J. Ash, "Encyclopedia of Surfactants", vol. I–III, Chemical Publishing Co., New York, NY, USA 1980–1981.

The pesticidal compositions of the invention may comprise 0.1% to 95%, preferably 0.1% to 80% of at least one compound of formula I or Ia, 1% to 99.9% of a solid or liquid adjuvant and 0% to 25%, preferably 0.1% to 25%, of a tenside.

Examples of the compositions of the invention are:
Emulsion Concentrates:
Active ingredient: 1% to 20%, preferably 5% to 10%
Surface-active substance: 5% to 30%, preferably 10% to 20%
Liquid carrier: 50% to 94%, preferably 70% to 85%
Suspension-Concentrates:
Active ingredient: 5% to 75%, preferably 10% to 50%
Water: 94% to 24%, preferably 88% to 30%
Surface-active substance: 1% to 40%, preferably 2% to 30%
Wettable Powder:
Active ingredient: 0.5% to 90%, preferably 1% to 80%
Surface-active substance: 0.5% to 20%, preferably 1% to 15%
Solid carrier: 5% to 95%, preferably 15% to 90%
Dusts:
Active ingredient: 0.1% to 10%, preferably 0.1% to 1%
Solid carrier: 99.9% to 90%, preferably 99.9% to 99%
Granulates:
Active ingredient: 0.5% to 30%, preferably 3% to 15%
Solid carrier: 99.5% to 70%, preferably 97% to 85%

As commodities the inventive fungicidal compositions may preferably be in a concentrated form whereas the end-user generally employs diluted compositions. Said compositions may be diluted to a concentration of 0.001% of active ingredient (a.i.). The doses usually are in the range of about 0.01 to 10 kg a.i./ha.

Said compositions may also comprise other auxiliaries such as stabilizers, defoamer, viscosity controlling agents, thickeners, adhesives, fertilisers or other active ingredients to obtain special effects.

For a more clear understanding of the invention, the following specific examples are set forth below. These examples are merely illustrations and are not to be understood as limiting the scope and underlying principles of the invention in any way. Indeed, various modifications of the invention in addition to those shown and described herein will become apparent to those skilled in the art from the following examples and foregoing description. Such modifications are also intended to fall within the scope of the appended claims. The term 1H-NMR as used in the examples hereinbelow designates proton nuclear magnetic resonance.

EXAMPLE 1

Preparation of 4-(N-Cyclohexylamidosulphonyl) phenylazoxycyanide 4-(N-Cyclohexylamido-sulphonyl)nitrosobenzene (178.9 g, 0.66 mole) is dissolved in 1,800 ml of dimethylformamide, treated with, 118.7 g (0.66 mole) of N-bromosuccinimide and stirred for 5 minutes at room temperature. A solution of 44.8 g (0.70 mole) of sodium cyanamide in 120 ml of water is added to the reaction mixture dropwise (20 minutes) with stirring, at about 25° C. The resultant orange red suspension is stirred for another 10 minutes and diluted with 5,000 ml of water. The mixture is filtered and the filtercake is washed twice with water and once with cold acetone to give the title product.

Yield 188 g (91.4 % of theory) of a beige powder, pure product (tlc); m. p. 171° C.

Mass (LC-MS): 308 [M⁺]

1H-NMR(DMSO-d⁶): 1.08 ppm; 1.42 ppm; 3.02 ppm [11 h, multiplet, cyclohexane ring];

8.06 ppm; 8.41 ppm [4H, phenyl, AA'BB']

The compounds listed in the following Tables 1 to 4 are prepared analogously to the product of Example 1.

TABLE 1

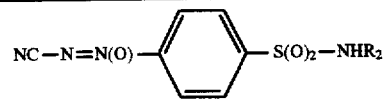

| No. | $R_2$ | m.p. [°C.] | yield (% of th.) | 1H—NMR (DMSO-d⁶) |
|---|---|---|---|---|
| 1 | cyclopropyl | 160–2 | 26.0 | |
| 2 | cyclobutyl | | | |
| 3 | cyclopentyl | 145 | 54.4 | 1.20 ppm, 1.70 ppm, 3.45 ppm [9H, multiplet, cyclopentane ring] 8.02 ppm, 8.42 ppm [4H, phenyl] |
| 4 | cycloheptyl | 128 | 42 | 1.15 ppm, 1.70 ppm, 3.20 ppm [13H, multiplet, cycloheptane ring]; |

TABLE 1-continued

NC—N=N(O)—⟨phenyl⟩—S(O)₂—NHR₂

| No. | R₂ | m.p. [°C.] | yield (% of th.) | 1H—NMR (DMSO-d⁶) |
|---|---|---|---|---|
| 5 | cyclooctyl | 128 | 42 | 8.04 ppm, 8.40 ppm [4H, phenyl] 1.15 ppm, 1.60 ppm; 3.25 ppm [15H, multiplet, cyclooctane ring] |
| 6 | 4-methyl-cyclohexyl | 109–20 | 52.7 | 8.02 ppm, 8.40 ppm [4H, phenyl ring] 0.89 ppm, 0.92 ppm [3H, 2 isomeric methyl groups] 1.05 ppm, 1.70 ppm, 3.25 ppm [10H, multiplet, cyclohexane ring] 8.05 ppm, 8.41 ppm [4H, phenyl ring] |
| 7 | 2,4,6-tri-methylcyclo-hexyl | | | |
| 8 | 3-ethyl-cyclopentyl | | | |
| 9 | 4-i-propyl-cyclohexyl | | | |
| 10 | 2-methyl-cyclohexyl | 143–6 | 48.0 | |
| 11 | 3-t-butyl-cyclopentyl | | | |
| 12 | 4-t-butyl-cyclohexyl (isomer 1*) | 184–7 | | |
| 13 | 4-t-butyl-cyclohexyl (isomer 2*) | 216–9 | | |
| 14 | 1-tetralinyl | 136–8 | 21 | 1.55 ppm, 1.85 ppm, 2.62 ppm, 4.40 ppm [7H, cyclohexane ring, multiplet]; 7.08 ppm, 8.10 ppm, 8.45 ppm [8H, aromatic protons] |
| 15 | 2,5-dimethyl-cyclopentyl | | | |
| 16 | 2-n-propyl-cyclopentyl | | | |

*Compounds no. 12 and 13 are stereoisomers.

TABLE 2

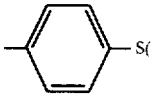

NC—N=N(O)—⟨X-phenyl⟩—S(O)₂—NR₁R₂

| No. | R₁ | R₂ | X |
|---|---|---|---|
| 1 | ethyl | cyclopropyl | H |
| 2 | methyl | cyclobutyl | H |
| 3 | ethyl | cyclopentyl | H |
| 4 | H | cycloheptyl | 3-Cl |
| 5 | H | cyclooctyl | 2-methyl |
| 6 | H | 4-methyl-cyclohexyl | 3-methyl |
| 7 | H | 2,4,6-tri-methylcyclo-hexyl | 3-Cl |
| 8 | methyl | 3-ethylcyclo-pentyl | 3-methyl |
| 9 | methyl | 4-i-propyl-cyclohexyl | H |
| 10 | n-propyl | 2-methyl-cyclohexyl | H |
| 11 | H | 3-t-butyl-cyclopentyl | 2-i-butyl |
| 12 | methyl | 4-t-butyl-cyclohexyl | H |
| 13 | H | 4-t-butyl-cyclohexyl | 2-methyl |
| 14 | H | 1-tetralinyl | 2-Cl |
| 15 | H | cyclohexyl | 2-Cl |
| 16 | H | cyclohexyl | 3-Cl |
| 17 | H | 2,5-dimethyl-cyclopentyl | 3-n-butyl |

TABLE 3

NC—N=N(O)—⟨X-phenyl, 3-S(O)₂—NR₁R₂⟩

| No. | R₁ | R₂ | X |
|---|---|---|---|
| 1 | H | cyclopropyl | 4-methyl |
| 2 | H | cyclopentyl | H |
| 3 | methyl | cyclohexyl | H |
| 4 | H | 2-methyl-cyclohexyl | H |
| 5 | H | cyclooctyl | 5-Cl |
| 6 | ethyl | 3-ethyl-cyclopentyl | 6-methyl |
| 7 | methyl | cyclohexyl | 4-Cl |

TABLE 4

NC—N=N(O)—⟨X-phenyl, 2-S(O)₂—NR₁R₂⟩

| No. | R₁ | R₂ | X |
|---|---|---|---|
| 1 | H | cyclopropyl | 4-methyl |
| 2 | methyl | cyclopentyl | H |
| 3 | H | cyclohexyl | H |
| 4 | H | 2-methyl-cyclohexyl | H |
| 5 | H | cyclooctyl | 5-Cl |
| 6 | ethyl | 3-ethyl-cyclopentyl | 6-methyl |
| 7 | methyl | cyclohexyl | H |
| 8 | methyl | cyclohexyl | 4-Cl |

EXAMPLE 2

Fungicidal Evaluation of Test Compounds

The fungicidal activity of the test compounds are investigated by means of the following tests.

1. Grape downy mildew on grape vine (*Plasmopara viticola* on vine)

Grape vine cuttings of the cultivar Muller-Thurgau are grown in the greenhouse at 25° C. and 50–70% relative humidity. When 6–7 leaves have developed, the plants are cut back to three leaves of equal size, one day before starting treatment.

The test compounds are dissolved in acetone with 0.5% Triton X155 at a concentration of 0.5%. Prior to application, the stock solution is diluted with demineralised water to give the final concentration of 200 ppm. The test plants are sprayed to near run-off in a spray cabinett using 20 ml of spray wash.

Three days later, the plants are artificially inoculated with an aqueous sporangial suspension of *Plasmopara viticola* containing 500,000 sporangia/ml. The inoculation is accomplished by spraying the underside of the leaves with the sporangial suspension. The inoculated plants are incubated in moist chambers at 100% humidity in darkness for 48 hours, then kept at high humidity (80–100%) in the greenhouse at 23° C. day- and 18° C. night-temperature until sporulation occurs.

The evaluation is carried out by estimating the percentage of diseased leaf area of each individual leaf. The fungicidal activity is reported as % disease control, in Table A.

TABLE A

| EFFECT AGAINST GRAPE DOWNY MILDEW | |
|---|---|
| Test Compound | % Disease Control |
| Example 1 | 95 |
| Table 1 No. 1 | 96 |
| Table 1 No. 3 | 98 |
| Table 1 No. 4 | 97 |
| Table 1 No. 5 | 100 |
| Table 1 No. 6 | 100 |
| Table 1 No. 10 | 100 |
| Table 1 No. 12 | 42 |
| Table 1 No. 14 | 98 |

What is claimed is:

1. A compound of the formula (I):

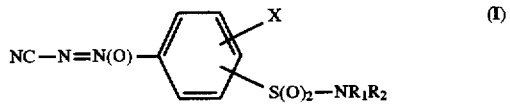

wherein $R_1$ represents a hydrogen atom or a $C_1$–$C_4$alkyl group;

$R_2$ represents a $C_3$–$C_8$cycloalkyl group, which may be substituted by one to three $C_1$–$C_6$alkyl groups or may be condensed with a benzene or a cyclohexane ring; and X represents a hydrogen, fluorine, chlorine or bromine atom or a $C_1$–$C_6$alkyl group.

2. The compound of claim 1, wherein X represents a hydrogen atom.

3. The compound of claim 1, wherein $R_1$ represents a hydrogen atom.

4. The compound of claim 1, wherein $R_1$ and X each represent a hydrogen atom.

5. The compound of claim 4 selected from the group consisting of 4-(N-cyclopropylamidosulphonyl)phenylazoxycyanide;
4-(N-cyclobutylamidosulphonyl)phenylazoxycyanide;
4-(N-cyclopentylamidosulphonyl)phenylazoxycyanide;
4-(N-cyclohexylamidosulphonyl)phenylazoxycyanide;
4-(N-cycloheptylamidosulphonyl)phenylazoxycyanide;
4-(N-cyclooctylamidosulphonyl)phenylazoxycyanide;
4-(N-4-methylcyclohexylamidosulphonyl)phenylazoxycyanide;
4-(N-1-tetralineamidosulphonyl)phenylazoxycyanide; and
4-(N-methyl-N-cyclohexylamidosulphonyl)phenylazoxycyanide.

6. A compound of the formula Ia:

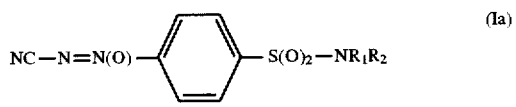

wherein $R_1$ represents a hydrogen atom or a $C_1$–$C_4$alkyl group; and $R_2$ represents a $C_3$–$C_8$cycloalkyl group, which may be substituted by one to three $C_1$–$C_6$alkyl groups or may be condensed with a benzene or a cyclohexane ring.

7. An antimicrobial composition of claim 1 having an antimicrobially effective amount of the compound of formula I.

8. The antimicrobial composition of claim 7, wherein X represents a hydrogen atom.

9. A fungicidal composition of claim 1, having a fungicidally effective amount of the compound of formula I and an agriculturally acceptable carrier.

10. The fungicidal composition of claim 9, wherein X represents a hydrogen atom.

11. The fungicidal composition of claim 9, wherein $R_1$ represents a hydrogen atom.

12. The fungicidal composition of claim 9, wherein $R_1$ and X each represent a hydrogen atom.

13. The fungicidal composition of claim 12, selected from the group consisting of 4-(N-cyclopropylamidosulphonyl)phenylazoxycyanide;
4-(N-cyclobutylamidosulphonyl)phenylazoxycyanide;
4-(N-cyclopentylamidosulphonyl)phenylazoxycyanide;
4-(N-cyclohexylamidosulphonyl)phenylazoxycyanide;
4-(N-cycloheptylamidosulphonyl)phenylazoxycyanide;
4-(N-cyclooctylamidosulphonyl)phenylazoxycyanide;
4-(N-4-methylcyclohexylamidosulphonyl)phenylazoxycyanide;
4-(N-1-tetralineamidosulphonyl)phenylazoxycyanide; and
4-(N-methyl-N-cyclohexylamidosulphonyl)phenylazoxycyanide.

14. A fungicidal composition of claim 6, having a fungicidally effective amount of the compound of formula Ia.

15. A method for combating an undesired microorganism, which comprises treating a locus infected therewith with the antimicrobial composition of claim 7.

16. A method for combating a phytopathogenic fungi, which method comprises contacting the phytopathogenic fungi with a fungicidally effective amount of the composition of claim 9.

17. The method according to claim 16 wherein $R_1$ and X each represent a hydrogen atom.

18. A process for the preparation of a compound of formula I

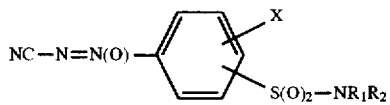 (I)

wherein $R_1$ represents a hydrogen atom or a $C_1$–$C_4$alkyl group; $R_2$ represents a $C_3$–$C_8$cycloalkyl group, which may be substituted by one to three $C_1$–$C_6$alkyl groups or may be condensed with a benzene or a cyclohexane ring; and X represents a hydrogen, fluorine, chlorine or bromine atom or a $C_1$–$C_6$alkyl group, the process comprising treating a nitroso compound of formula II

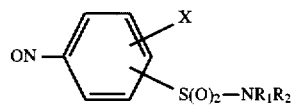 (II)

with N-bromosuccinimide and with sodium cyanamide.

* * * * *